United States Patent [19]

Dereu et al.

[11] Patent Number: 4,730,053

[45] Date of Patent: Mar. 8, 1988

[54] S-[2-PHENYL (ALKYL) CARBAMOYL]-PHENYLSELENYLMERCAPTO DERIVATIVES

[75] Inventors: Norbert Dereu, Frechen-Bachem; Albrecht Wendel, Tübingen; Helmut Sies, Düsseldorf; Sigurd Leyck, Pulheim; Axel Römer, Hürth-Gleuel; Erich Graf, Kerpen-Horrem, all of Fed. Rep. of Germany

[73] Assignee: A. Nattermann & Cie GmbH, Cologne, Fed. Rep. of Germany

[21] Appl. No.: 801,561

[22] Filed: Nov. 25, 1985

[30] Foreign Application Priority Data

Nov. 29, 1984 [DE] Fed. Rep. of Germany ....... 3443467

[51] Int. Cl.[4] .................. C07C 163/00; A61K 31/44; A61K 31/165
[52] U.S. Cl. ........................... 546/337; 260/550; 514/347; 514/357; 514/522; 514/533; 514/535; 514/539; 514/562; 514/618; 546/330; 546/335; 558/415; 560/9; 560/16; 560/18; 562/426; 562/432
[58] Field of Search .................. 562/426, 432; 564/162; 560/9, 16, 18; 546/294, 337, 330, 335; 558/415; 514/347, 357, 522, 533, 535, 539, 562, 618; 260/550

[56] References Cited

U.S. PATENT DOCUMENTS

| | | | |
|---|---|---|---|
| 4,352,799 | 10/1982 | Renson et al. | 514/183 |
| 4,418,069 | 11/1983 | Welter et al. | 514/359 |
| 4,618,669 | 10/1986 | Dereu et al. | 562/426 X |

FOREIGN PATENT DOCUMENTS 0098934  1/1984  European Pat. Off. ........... 260/550

OTHER PUBLICATIONS

Fundamental and Applied Toxicology (3) 9-10 (1983), pp. 431-436, Reddy et al.
Agents and Actions, Supp. 7, pp. 214-219, Bragt et al.
Methods of Enzymology, vol. 77, pp. 325-333 (1981), Wendel.
Free Radicals in Biology, vol. V, pp. 223-254, Leopold Flohe.

Primary Examiner—Donald B. Moyer
Assistant Examiner—Patricia M. Scott
Attorney, Agent, or Firm—Pearne, Gordon, McCoy & Granger

[57] ABSTRACT

The present invention is related to new S-(Carbamoylphenylselenyl) derivatives of mercaptanes of the general formula (I)

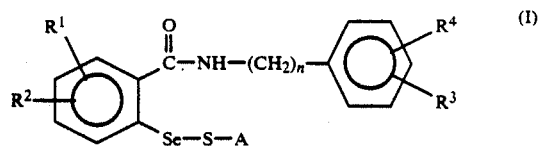

and to a process for the treatment of diseases caused by cell injury due to the increased formation of active oxygen metabolites.

4 Claims, No Drawings

S-[2-PHENYL (ALKYL) CARBAMOYL]-PHENYLSELENYLMERCAPTO DERIVATIVES

The present invention is related to new S-(carbamoyl-phenylselenyl) derivatives of aliphatic and aromatic mercaptanes, which are characterized by valuable pharmacological properties. They are used in humans for the treatment of diseases caused by a cell injury due to the increased formation of active oxygen metabolites, such as liver defects, cardiac infarction, inflammations, radiation defects.

The compounds of the present invention correspond to the general formula (I)

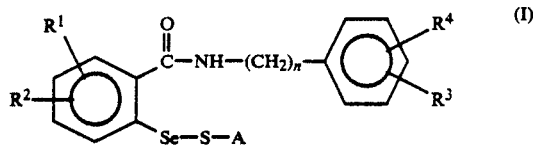

wherein $R^1$, $R^2$, $R^3$ and $R^4$ are identical or different and independently represent hydrogen, halogen, $C_{1-4}$-alkyl, $C_{1-3}$-alkoxy, hydroxy, trifluoromethyl, nitro, cyano, carboxy, $C_{1-2}$-alkoxycarbonyl, carboxy-$C_{1-4}$-alkyl, $C_{1-2}$-alkoxycarbonyl-$C_{1-4}$-alkyl and A represents a straight or branched alkyl group having 1 to 4 carbon atoms which can be substituted by 1 to 3 carboxy, hydroxy, mercapto, carboxyalkylcarbamoyl groups, wherein an esterification of the functional modificable carboxyl group with a $C_{1-3}$-alcohol is possible, or a phenyl, carboxyphenyl, alkoxycarbonylphenyl, pyridyl or pyridylalkyl group and n is zero or one.

Halogen means fluorine, chlorine, bromine. Alkyl groups having 1 to 4 carbon atoms are methyl, ethyl, propyl, isopropyl, butyl, isobutyl, sec-butyl, tert-butyl. Alkoxy groups having 1 to 3 carbon atoms are methoxy, ethoxy, propoxy.

Preferred are compounds wherein $R^1$, $R^2$, $R^3$, $R^4$ are identical or different and independently represent hydrogen, fluorine, chlorine, methyl, methoxy, hydroxy, trifluoromethyl, cyano, carboxy, $C_{1-2}$-alkoxycarbonyl, carboxy-$C_{1-4}$-alkyl, $C_{1-2}$-alkoxycarbonyl-$C_{1-4}$-alkyl or nitro. Particularly preferred are compounds wherein $R^1$, $R^2$ are identical or different and independently represent hydrogen, fluorine, chlorine, methyl, methoxy, hydroxy, trifluoromethyl or nitro, while $R^3$, $R^4$ represent hydrogen, methoxy or hydroxy. A corresponds to the rest of the mercapto compound used for the reaction, such as ethylmercaptane, mercapto-acetic acid, 2-mercaptopropionic acid, 3-mercaptopropionic acid, mercapto-acetic acid methylester, mercaptoacetic acid ethylester, 2-mercaptopropionic acid methylester, 3-mercaptopropionic acid methylester, 2-mercaptopropionylglycine, 2-mercaptopropionylglycinethylester, mercaptosuccinic acid, 3-mercapto-1,2-propanediol, threo-1,4-dimercapto-2,3-butanediol, thiophenol, thiosalicyclic acid, thiosalicylic acid methylester, 2-mercaptopyrdine, 3-mercaptomethylpyridine.

Compounds of formula (I) comprising a chirality center can be present as racemates or in form of D- or L-enantiomers dependent on the starting materials. If a separation of the racemates is desired, it can be carried out conveniently using processes known per se with suitable optical active bases through the formation of diastereomeric salts or by chromatography using an optical active column material.

Examples for the compounds of the present invention are:

S-(2-phenylcarbamoyl-phenylselenyl)-ethylmercaptane
S-[2-(2-fluorophenylcarbamoyl)-phenylselenyl]-ethylmercaptane
S-(2-phenylcarbamoyl-phenylselenyl)-mercapto-acetic acid ethylester
S-(2-phenylcarbamoyl-phenylselenyl)-3-mercaptopropionic acid
S-(2-phenylcarbamoyl-6-methoxy-phenylselenyl)-3-mercaptopropionic acid
S-(2-phenylcarbamoyl-phenylselenyl)-DL-2-mercaptopropionylglycine
S-(2-phenylcarbamoyl-phenylselenyl)-DL-2-mercaptopropionylglycineethylester
S-[2-(3-fluorophenylcarbamoyl)-phenylselenyl]-DL-2-mercaptopropionylglycine
S-[2-(4-methoxyphenylcarbamoyl)-phenylselenyl]-DL-2-mercaptopropionylglycine
S-(2-phenylcarbamoyl-5-chloro-phenylselenyl)-DL-2-mercaptopropionylglycine
S-(2-phenylcarbamoyl-6-methoxy-phenylselenyl)-DL-2-mercaptopropionylglycine
S-[2-(4-nitrophenylcarbamoyl)-phenylselenyl]-DL-2-mercaptopropionylglycine
S-2-(4-chlorophenylcarbamoyl)-phenylselenyl]-DL-2-mercaptopropionylglycine
S-(2-phenylcarbamoyl-phenylselenyl)-3-mercaptopropionylglycine
S-(2-phenylcarbamoyl-phenylselenyl)-3-mercaptopropionylglycineethylester
S-(2-phenylcarbamoyl-6-methoxy-phenylselenyl)-3-mercaptopropionylglycine
S-[2-(4-nitrophenylcarbamoyl)-phenylselenyl]-3-mercaptopropionylglycine
S-(2-phenylcarbamoyl-phenylselenyl)-DL-mercaptosuccinic acid
S-[2-(3-fluorophenylcarbamoyl)-phenylselenyl]-DL-mercaptosuccinic acid
S-[2-(4-methoxyphenylcarbamoyl)-phenylselenyl]-DL-mercaptosuccinic acid
S-(2-phenylcarbamoyl-5-chlor-phenylselenyl)-DL-mercaptosuccinic acid
S-(2-phenylcarbamoyl-6-methoxy-phenylselenyl)-DL-mercaptosuccinic acid
S-[2-(4-nitrophenylcarbamoyl)-phenylselenyl]-DL-mercaptosuccinic acid
S-[2-(4-chlorophenylcarbamoyl)-phenylselenyl]-DL-mercaptosuccinic acid
S-[2-(4-chlorophenylcarbamoyl)-6-methoxy-phenylselenyl]-DL-mercaptosuccinic acid
S-[2-(4-nitrophenylcarbamoyl)-6-methoxy-phenylselenyl]-DL-mercaptosuccinic acid
S-[2-(3,4-dichlorophenylcarbamoyl)-6-methoxy-phenylselenyl]-DL-mercaptosuccinic acid
S-[2-(3,4-difluorophenylcarbamoyl)-6-methoxy-phenylselenyl]-DL-mercaptosuccinic acid
S-[2-(3-chloro-4-methoxy-phenylcarbamoyl)-6-methoxy-phenylselenyl]-DL-mercaptosuccinic acid
S-[2-(3,4-dimethoxyphenylcarbamoyl)-6-methoxy-phenylselenyl]-DL-mercaptosuccinic acid
S-[2-(4-chloro-3-fluoro-phenylcarbamoyl)-6-methoxy-phenylselenyl]-DL-mercaptosuccinic acid S-[2-(4-methoxy-3-methyl-phenylcarbamoyl)-6-methoxy-phenylselenyl]-DL-mercaptosuccinic acid S-[2-(4-methoxy-2-nitro-phenylcarbamoyl)-6-methoxy-phenylselenyl]-DL-mercaptosuccinic acid S-(2-phenylcarbamoyl-phenylselenyl)-DL-threo-1,4-dimercapto-2,3-butanediol S-(2-benzylcarbamoyl-phenylselenyl)-mercaptoacetic acid S-(2-benzylcarbamoyl-6-methoxy-phenylselenyl)-mercaptoacetic acid S-(2-benzylcarbamoyl-6-methoxy-phenylselenyl)-DL-2-mercaptopropionic acid S-(2-benzylcarbamoyl-phenylselenyl)-DL-2-mercaptopropionylglycine S-(2-benzylcarbamoyl-6-methoxy-phenylselenyl)-DL-2-mercaptopropionylglycine S-(2-benzylcarbamoyl-phenylselenyl)-3-mercaptopropionylglycine S-(2-benzylcarbamoyl-6-methoxy-phenylselenyl)-3-mercaptopropionylglycine S-(2-phenylcarbamoyl-phenylselenyl)-thiophenol S-[2-(4-nitrophenylcarbamoyl)-phenylselenyl]-thiophenol S-(2-phenylcarbamoyl-phenylselenyl)mercaptosalicylic acid S-(2-phenylcarbamoyl-phenylselenyl)-mercaptosalicylic acid methylester S-(2-phenylcarbamoyl-phenylselenyl)-2-mercaptopyridine The substances of the present invention exhibit glutathioneperoxidase-like properties and are able to replace this enzyme and to prevent in this way, in cooperation with mercaptanes (f.e. glutathione), the harmful effect of active oxygen metabolites.

The selenium dependent glutathione(GSH)-peroxidase(Px) catalyzes the reduction of $H_2O_2$ and of organic hydroperoxides:

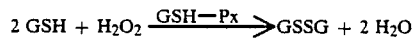

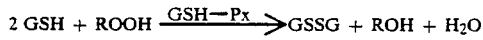

The selenium containing enzyme protects the cells against the peroxidation and plays an important role in the modulation of the arachidonic acid metabolism (C. C. Reddy, E. J. Massaro, Fundam. and Appl. Toxicology (3), 9–10(1983), pages 431–436, and L. Flohé, Free Radicals in Biology, Vol. V, edited by W. A. Pryor 1982, Academic Press, pages 223–254).

The glutathione peroxidase plays a role in all diseases wherein a cell injury of the respective tissue and finally a necrose results due to an increased formation of active oxygen metabolites in form of peroxides (such as lipoid peroxides and hydrogen peroxide). This so-called "oxidative stress" can for example be seen in liver diseases—induced by inflammative or autoimmunologic reactions, by alcohol or by medicaments—but also in other diseases, for example the cardiac infarction. It is known, that after a cardiac infarction, leucocytes migrate into the injured area and the cell destruction is accompanied by an increased releasing of the above named oxygen metabolites. Finally, this leads to a progressive decomposition of the tissue.

In such cases, the important and naturally existing protecting system consisting of various peroxides and active oxygen decompositing enzymes is overloaded. This includes superoxide dismutase, catalase, and particularly the glutathione-redox-system with the respective enzyme component glutathione-peroxidase. The latter principal is of a great importance, since it is capable of depoisoning both organic peroxides and hydrogen peroxide. It is confirmed that this system plays an important role for the intact liver function (Wendel et al, Biochemical Pharmacology, Vol. 31, page 3601 (1982)) and that for example the extent of an experimetal liver injury is dependent on this system, i.e. on the content of the liver of glutathione on one side and on the activity of the enzyme glutathione-peroxidase on the other side. In the course of a generic inflammation, this liver protection mechanism is essentially reduced (Bragt et al, Agents and Actions, Supp. 7, page 214 (1980)), whereby the liver suffers from an essentially increased "oxidative stress".

A very important role is played by the reactive oxygen metabolites as mediators of inflammations. They seem to take part in leucotaxis, vessel permeability, injuries of connective tissue, psoriasis and immunocomplex/complement induced effects as well as in injuries caused by reflowing into ischemic areas (L. Flohé et al, The Pharmacology of Inflammation, ed. IL. Bonta et al, Handbook of Inflammation, vol. 5, Elsevier, Amsterdam, pages 255–270).

Also the injuries after ionizing radiation are caused by the formation of radicals and of active oxygen metabolites. A route for the chemical cytoprotection therefore is a strengthening of the glutathione/glutathioneperoxidase system.

The measuring of the glutathione peroxidase activity was carried out according to the method of A. Wendel (A. Wendel, Methods in Enzymology, vol. 77, 325–333 (1981)). In this experiment, the mercaptane concentration is measured by means of Ellmans Reagent.

The reducing agent in this case is not glutathione, but the mercaptane containing substance which has been used for the synthesis of the respective compound. Surprisingly, now it has been found that the compounds of the present invention of formula I possess a glutathioneperoxidase-like activity. The reaction of the benzoisoselenazolones with mercaptanes proceeds in the example of 2-phenyl-1,2-benzoisoselenazole-3,(2H)-one according to the following equation:

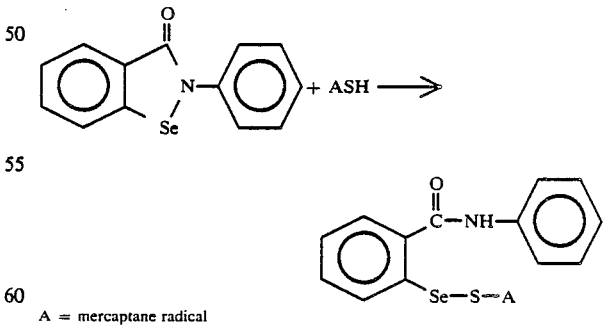

A = mercaptane radical

GLUTATHIONEPEROXIDASE-LIKE ACTIVITY

In in-vitro experiments, the catalysis of the peroxidase destruction has been examined. It was found, that the compounds of the present invention can replace the glutathioneperoxidase.

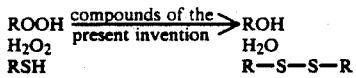

The reaction rates were measured by the method of A. Wendel (A. Wendel, Methods in Enzymology, vol. 77, pages 325-333 (1981)). As a reference substance, S-(2-phenylcarbamoylphenylselenyl)-glutathione was used. In the presence of a 1 mmolar concentration of glutathione with tert-butylhydroperoxide a reaction rate of $1,17 \times 10^6$ units per mol is obtained. This activity is taken as 100% for comparative purposes.

| | Catalytic Activity (%) |
|---|---|
| S—(2-phenylcarbamoyl-phenylselenyl)-DL-threo-1,4-dimercapto-2,3-butanediol | 390 |
| S—(2-phenylcarbamoyl-phenylselenyl)-thiophenol | 28 |
| S—(2-phenylcarbamoyl-phenylselenyl)-3-mercaptopropionic acid | 47 |
| S—(2-phenylcarbamoyl-phenylselenyl)-mercaptoacetic acid ethylester | 330 |
| S—[2-(4-nitrophenylcarbamoyl)-phenylselenyl]-thio-phenol | 67 |
| S—(6-methoxy-2-phenylcarbamoyl)-phenylselenyl-DL-threo-1,4-dimercapto-2,3-butanediol | 580 |

The compounds of the present invention also inhibit the edema of the rat paw induced by the cobra venum factor.

As determination serves the method of S. Leyck, E. Etschenberg, V. Hadding and J. Winkelmann, Agents and Actions, vol. 13, 5/6 (1983).

To induce an edema, the cobra venum factor is injected in a volume of 0,1 ml water subplantar into the left back paw of Han-Vistar rats of both sexes having a weight of 150–200 g.

The determination of the edema is carried out plethismographically directly before and 3 hours after the induction of the edema. The obtained difference values of the single groups are measured and the change in percent based on untreated controls is determined. The results are listed in the following table:

| Substance | Antiinflammation activity in % Dose 100 mg/kg i.m. |
|---|---|
| S—(2-phenylcarbamoyl-phenylselenyl)-ethylmercaptane | −32 |
| S—(2-phenylcarbamoyl-phenylselenyl)-DL-2-mercaptopropionylglycine | −71 |
| S—(2-phenylcarbamoyl-phenylselenyl)-DL-mercaptosuccinic acid | −84 |
| S—[2-(4-nitrophenylcarbamoyl)-phenylselenyl]-thiophenol | −20 |
| S—(2-phenylcarbamoyl-phenylselenyl)-3-mercaptopropionic acid | −52 |
| S—(2-phenylcarbamoyl-phenylselenyl)-thiophenol | −25 |

The preparation of the compounds of the present invention is carried out by reacting 1,2-benzisoselenazolones of the formula II obtained according to the prescriptions of U.S. Pat. No. 4,352,711, DE-OS No. 30 27 074 and U.S. Pat. No. 4,418,069, respectively, with mercaptanes:

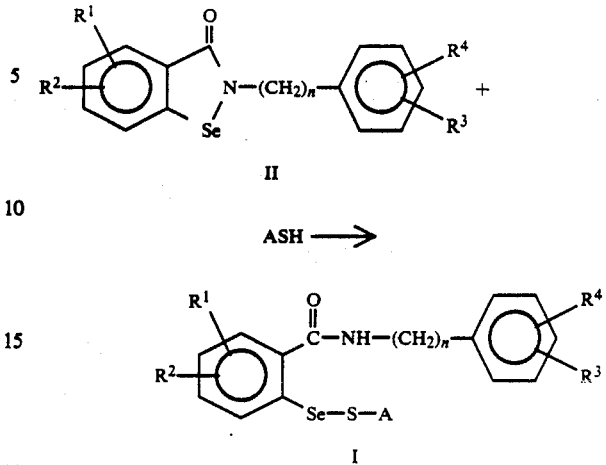

The reaction with the respective mercaptane is carried out either in suspensions of 1,2-benzisoselenazolones in chlorinated hydrocarbons like chloroform, dichloromethane, dichloroethane or in a trifluoroacetic acid solution while stirring at room temperature within 12–24 hours. The mercaptanes used for the reaction are known compounds.

The present invention also refers to pharmaceutical preparations containing compounds of the formula I. The pharmaceutical preparations of the present invention are such ones for the enteric like oral or rectal as well as parenteric administration containing the pharmaceutically active compounds alone or together with a common pharmaceutically acceptable support material. Conveniently, the pharmaceutical preparation of the active component is present in form of single doses adapted to the desired administration, such as tablets, dragees, capsules, suppositories, granulate, solutions, emulsions or suspensions. The dosage of the substances normally lies within 10 and 1000 mg per day, preferably between 30 and 300 mg per day, most preferably between 50 and 150 mg per day, and the administration can be made in a single dose or in a plurality of partial doses, preferably in two to three partial doses per day.

The preparation of the compounds of the present invention is illustrated in detail in the following examples. The melting points indicated therein were measured using a Büchi 510-melting point measurement apparatus and are indicated in centigrade and not corrected.

EXAMPLE 1

S-(2-phenylcarbamoyl-phenylselenyl)-ethylmercaptane 5 g (18,2 mmol) of 2-phenyl-1,2-benzisoselenazole-3(2H)-one are suspended in 150 ml chloroform (only partly soluble). 2 g (32,2 mmol) ethylmercaptane are added dropwise to this suspension. A clear solution is obtained and the stirring is continued overnight. The solvent is evaporated and the residue is treated with 100 ml hexane. The obtained cristals are sucked off and washed with 50 ml hexane.

Yield: 5,2 g (85% of the theory), melting point (m.p. 127°–129° C.)

EXAMPLE 2

S-(2-phenylcarbamoyl-phenylselenyl)-mercaptosalicylic acid

Prepared similar to example 1 from 5 g (18,2 mmol) of 2-phenyl-1,2-benzisoselenazole-3(2H)-one and 2,8 g (18,2 mmol) of mercaptosalicylic acid.

Yield: 5 g (64,3% of the theory), m.p. 239°–241° C.

EXAMPLE 3

S-(2-phenylcarbamoyl-phenylselenyl)-mercaptosalicylic acid methyl ester

Prepared similar to example 1 from 5 g (18,2 mmol) of 2-phenyl-1,2-benzisoselenazole-3(2H)-one and 3,1 g (18,4 mmol) of mercaptosalicylic acid methyl ester.

Yield: 7,25 g (90% of the theory), m.p. 138°–140° C.

EXAMPLE 4

S-(2-phenylcarbamoyl-phenylselenyl)-3-mercaptopropionic acid

Prepared similar to example 1 from 5 g (18,2 mmol) of 2-phenyl-1,2-benzisoselenazole-3(2H)-one and 2 g (18,9 mmol) of 3-mercaptopropionic acid.

Yield: 5,85 g (85% of the theory), m.p. 203°–204° C.

EXAMPLE 5

S-(2-phenylcarbamoyl-phenylselenyl)-mercaptoacetic acid ethyl ester

Prepared similar to example 1 from 2 g (7,3 mmol) of 2-phenyl-1,2-benzisoselenazole-3(2H)-one and 1 g (8,3 mmol) of mercaptoacetic acid ethyl ester.

Yield: 2,4 g (84% of the theory), m.p. 92°–94° C.

EXAMPLE 6

S-(2-phenylcarbamoyl-phenylselenyl)-DL-2-mercaptopropionylglycine 1 g (3,65 mmol) of 2-phenyl-1,2-benzisoselenazole-3(2H)-one and 0,6 g (3,68 mmol) of DL-2-mercaptopropionylglycine are dissolved in 15 ml trifluoroacetic acid and the stirring is continued for 18 hours at room temperature. Then, 100 ml of an ice/water mixture is added to the solution. The obtained precipitate is extracted with dichloromethane. After drying the solvent and evaporating in vacuum, the solid is then recristallized from ethanol/water (7:3).

Yield: 1,5 g (94% of the theory), m.p. 199° C.

EXAMPLE 7

S-(2-phenylcarbamoyl-phenylselenyl)-2-mercaptopyridine

Prepared similar to example 1 from 2,5 g (9,1 mmol) of 2-phenyl-1,2-benzisoselenazole-3(2H)-one and 1,2 g (10,8 mmol) of 2-mercaptopyridine.

Yield: 3,2 g (91,1% of the theory), m.p. 67° C. (decomposition)

EXAMPLE 8

S-[2-(4-nitrophenylcarbamoyl)-phenylselenyl]-thiophenol

Prepared similar to example 1 from 5 g (15,7 mmol) of 2-(4-nitrophenyl)-1,2-benzisoselenazole-3(2H)-one and 1,75 g (15,9 mmol) thiophenol.

Yield: 5,7 g (84,8% of the theory), m.p. 60° C. (decomposition)

EXAMPLE 9

S-[2-(3-fluorophenylcarbamoyl)-phenylselenyl]-ethylmercaptane

Prepared similar to example 1 from 5 g (17,1 mmol) of 2-(3-fluorophenyl)-1,2-benzisoselenazole-3(2H)-one and 2,2 g (35,5 mmol) of ethylmercaptane.

Yield: 3,9 g (64,3% of the theory), m.p. 93°–95° C.

EXAMPLE 10

S-(2-phenylcarbamoyl-phenylselenyl)-DL-mercaptosuccinic acid

Prepared similar to example 1 from 1 g (3,65 mmol) of 2-phenyl-1,2-benzisoselenazole-3(2H)-one and 0,55 g (3,66 mmol) DL-mercaptosuccinic acid.

Yield: 1,3 g (84% of the theory), m.p. 200° C. (decomposition)

EXAMPLE 11

S-(2-phenylcarbamoyl-phenylselenyl)-2-mercaptopropionylglycine

Prepared similar to example 1 from 2 g (7,3 mmol) of 2-phenyl-1,2-benzisoselenazole-3(2H)-one and 1,2 g (7,35 mmol) of 3-mercaptopropionylglycine.

Yield: 3,0 g (94% of the theory), m.p. 199° C.

EXAMPLE 12

S-(2-benzylcarbamoyl-phenylselenyl)-mercaptoacetic acid

Prepared similar to example 1 from 2,88 g (10,0 mmol) of 2-benzyl-1,2-benzisoselenazole-3(2H)-one and 0,95 g (10,3 mmol) mercaptoactic acid.

Yield: 0,95 g (25% of the theory), m.p. 145°–147° C.

EXAMPLE 13

S-(2-benzylcarbamoyl-phenylselenyl)-3-mercapto-1,2-propanediol

Prepared similar to example 1 from 2,88 g (10,0 mmol) of 2-benzyl-1,2-benzisoselenazole-3(2H)-one and 1,1 g (10,2 mmol) of 3-mercapto-1,2-propanediol.

Yield: 2,1 g (53% of the theory), m.p. 187° C.

EXAMPLE 14

S-(2-phenylcarbamoyl-phenylselenyl)-DL-threo-1,4-dimercapto-2,3-butanediol

Prepared similar to example 6 from 2,74 g (10 mmol) of 2-phenyl-1,2-benzisoselenazole-3(2H)-one and 1,55 g (10 mmol) of DL-threo-1,4-dimercapto-2,3-butanediol.

The purification of the substance is carried out by column chromatography.

Yield: 0,5 g (11,6% of the theory), m.p. 78°–82° C.

EXAMPLE 15

S-(2-phenylcarbamoyl-6-methoxy-phenylselenyl)-DL-2-mercaptopropionylglycine

Prepared similar to example 1 from 3,0 g (9,87 mmol) of 7-methoxy-2-phenyl-1,2-benzisoselenazole-3(2H)-one and 1,63 g (10 mmol) of DL-2-mercaptopropionylglycine.

Yield: 4,5 g (97,6% of the theory), m.p. 242°–245° C.

EXAMPLE 16

S-(2-phenylcarbamoyl-4-chloro-phenylselenyl)-ethylmercaptane

Prepared similar to example from 3,0 g (9,72 mmol) of 5-chloro-2-phenyl-1,2-benzisoselenazole-3(2H)-one and 1 g (15,9 mmol) of ethylmercaptane.

Yield: 3,1 g (86% of the theory), m.p. 163°–166° C.

What we claim is:

1. A compound of formula (I)

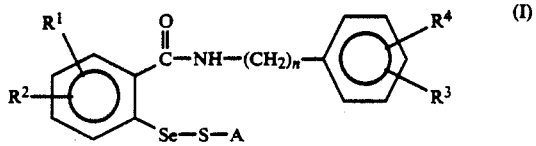

wherein $R^1$, $R^2$, $R^3$ and $R^4$ are identical or different from each other and represent members selected from the group consisting of hydrogen, halogen, $C_{1-4}$-alkyl, $C_{1-3}$-alkoxy, trifluoromethyl, nitro, cyano, hydroxy, carboxy, $C_{1-2}$-alkoxycarbonyl, carboxy-$C_{1-4}$-alkyl and $C_{1-2}$-alkoxycarbonyl-$C_{1-4}$-alkyl and A represents a member selected from the group constisting of the straight and branched alkyl groups having 1 to 4 carbon atoms and said alkyl groups substituted by 1 to 3 members selected from the group consisting of the carboxy, $C_{1-3}$-alkoxycarbonyl, hydroxy, mercapto, carboxy-$C_{1-4}$-alkylcarbamoyl, $C_{1-3}$-alkoxycarbonyl $C_{1-4}$-alkylcarbamoyl, phenyl, carboxyphenyl, $C_{1-3}$-alkoxycarbonylphenyl, pyridyl and pyridyl-$C_{1-4}$-alkyl groups, and n is zero or one.

2. A compound according to claim 1, wherein $R^1$, $R^2$, $R^3$ and $R^4$ are identical or different from each other and represent a member selected from the group consisting of hydrogen, fluorine, chlorine, methyl, methoxy, hydroxy, trifluoromethyl, nitro, cyano, carboxy, $C_{1-2}$-alkoxycarbonyl, carboxy-$C_{1-4}$-alkyl and $C_{1-2}$-alkoxycarbonyl-$C_{1-4}$-alkyl, and A represents a member selected from the group consisting of the straight and branched alkyl groups containing 1 to 4 carbon atoms and said groups substituted by 1 to 3 members selected from the group consisting of carboxy, $C_{1-2}$-alkoxycarbonyl, carboxy-$C_{1-4}$-alkylcarbamoyl, $C_{1-2}$-alkoxycarbonyl-$C_{1-4}$-alkylcarbamoyl, and phenyl, carboxyphenyl, $C_{1-12}$-alkoxycarbonylphenyl, pyridyl and pyridyl-$C_{1-4}$-alkyl, and n is zero or one.

3. A compound according to claim 1, wherein $R^1$ and $R^2$ are identical or different from each other and represent a member selected from the group consisting of hydrogen, fluorine, chlorine, methyl, methoxy, hydroxy, trifluoromethyl and nitro, and $R^3$ and $R^4$ are identical or different from each other and represent a member selected from the group consisting of hydrogen, fluorine, chlorine, ethoxy, hydroxy, cyano, carboxy, $C_{1-2}$-alkoxycarbonyl, carboxy-$C_{1-4}$-alkyl, $C_{1-2}$-alkoxycarbonyl-$C_{1-4}$-alkyl, and A represents a member selected from the group consisting of the straight and branched alkyl groups having 1 to 4 carbon atoms and said alkyl groups substituted by 1 to 3 members selected from the group consisting of carboxy, $C_{1-2}$-alkoxycarbonyl, hydroxy, mercapto, carboxy-$C_{1-4}$-alkylcarbamoyl and $C_{1-2}$ alkoxycarbonyl-$C_{1-4}$-alkylcarbamoyl and n is zero or one.

4. A compound according to claim 1, wherein $R^1$ and $R^2$ are identical or different from each other and represent a member selected from the group consisting of hydrogen, fluorine, chlorine, methyl, methoxy, hydroxy, trifluoromethyl, nitro, and $R^3$ and $R^4$ are identical or different from each other and represent a member selected from the group consisting of hydrogen, fluorine, chlorine, methoxy, hydroxy, cyano, carboxy, $C_{1-2}$-alkoxycarbonyl, carboxy-$C_{1-4}$-alkyl, $C_{1-2}$-alkoxy-carbonyl-$C_{1-4}$-alkyl, and A represents a member selected from the group consisting of the straight and branched alkyl groups having 1 to 4 carbon atoms and said alkyl groups substituted by 1 to 3 members selected from the group consisting of phenyl, carboxyphenyl, methoxycarbonylphenyl, pyridyl and pyridylmethyl, and n is zero or one.

* * * * *